US005756457A

United States Patent [19]

Wang et al.

[11] Patent Number: 5,756,457
[45] Date of Patent: May 26, 1998

[54] NEURAL REGENERATION USING HUMAN BONE MORPHOGENETIC PROTEINS

[75] Inventors: Elizabeth A. Wang, Carlisle; Josephine S. D'Alessandro, Marblehead, both of Mass.; Dean M. Toriumi, Riverside, Ill.

[73] Assignee: Genetics Institute, Inc., Cambridge, Mass.

[21] Appl. No.: 435,120

[22] Filed: May 5, 1995

Related U.S. Application Data

[63] Continuation-in-part of Ser. No. 112,492, Aug. 26, 1993, abandoned.

[51] Int. Cl.$^6$ .................................................... A61K 38/18
[52] U.S. Cl. .............................. 514/12; 606/152; 424/422; 424/423
[58] Field of Search ........................... 606/152–158; 623/11, 12; 514/12; 530/350, 399; 424/422, 423

[56] References Cited

U.S. PATENT DOCUMENTS

| 4,868,161 | 9/1989 | Roberts | 514/69 |
| 4,920,962 | 5/1990 | Proulx | 606/152 |
| 4,955,892 | 9/1990 | Daniloff et al. | 606/152 |
| 4,963,146 | 10/1990 | Li | 606/152 |
| 5,292,802 | 3/1994 | Rhee et al. | 525/54.1 |
| 5,306,307 | 4/1994 | Senter et al. | 623/17 |
| 5,308,889 | 5/1994 | Rhee et al. | 523/113 |
| 5,328,955 | 7/1994 | Rhee et al. | 525/54.1 |

FOREIGN PATENT DOCUMENTS

WO/9403200 2/1994 WIPO.

OTHER PUBLICATIONS

D'Alessandro, J. et al., *Growth Factors*, 11:53–69, 1994.
A. Bignami et al., *Brain Research* 43:429–435 (1972).
J.R. Fallon, *J. of Cell Biology*, 100: 198–207 (Jan. 1985).
Michel Kliot et al., *Experimental Neurology*, 109: 57–69 (1990).
Leu–Fen H. Lin et al., *Science*, 260: 1130–1132 (May 21, 1993).
Eldon E. Geisert Jr. et al., *Developmental Biology*, 143: 335–3455 (1991).
R. Goodman, "Methods for Serum–Fee Culture of Neuronal and Lymphoid Cells", 23–36 (1984).
Mark Noble et al., *J. of Neuroscience*, 4: No. 7 1892–1903 (1984).
G. Perides et al., *J. Biological Chemistry*, 269: No. 1 765–770 (Jan. 7, 1994).
George M. Smith et al., *Brain Research*, 543: 111–122 (1991).

*Primary Examiner*—Marianne P. Allen
*Attorney, Agent, or Firm*—Steven R. Lazar

[57] ABSTRACT

Methods and devices are disclosed for inducing growth of neural cells, and repairing neural defects in a mammal. The method comprises administering to said mammal at the site of neural defect, damage or depletion, an effective amount of a bone morphogenetic protein, either in admixture with a pharmaceutically acceptable vehicle, or adsorbed to a suitable matrix. The device comprises bone morphogenetic protein, optionally in combination with other factors, adsorbed on a suitable matrix and contained within an artificial nerve replacement vessel.

17 Claims, No Drawings

NEURAL REGENERATION USING HUMAN BONE MORPHOGENETIC PROTEINS

RELATED APPLICATIONS

The present application is a continuation-in-part of Ser. No. 08/112,492, filed on Aug. 26, 1993, which has been abandoned.

FIELD OF THE INVENTION

The present invention relates to pharmaceutical uses of bone morphogenetic proteins (BMPs) for proliferation of neural cells and for regeneration of nerve tissue. More particularly, the subject invention relates to the use of BMPs, preferably, BMP-2 through 10 for the treatment of central and peripheral nervous system diseases, as well as mechanical and traumatic disorders, which involve degeneration, death or trauma to neural cells or nerve tissue.

BACKGROUND

Bone morphogenetic proteins 2 through 10 are members of the transforming growth factor-β (TGF-β) superfamily. The BMPs were originally discovered as osteogenic proteins capable of inducing bone formation in vivo. The transforming growth factors were initially identified on the basis of their ability to induce phenotypic transformation of mammalian cells grown in tissue culture, a phenomenon which has traditionally been associated with in vivo changes from normal to tumor cell growth.

Astrocytes are a type of glial cell found in the nervous system which function in axonal guidance, stimulation of neurite outgrowth, neuron morphogenesis and migration. Astrocytes have also been implicated in induction of the vascular endothelial blood-brain barrier and transport of blood to the neurons. Astrocytes express an intermediate filament protein of the cytoskeleton, glial fibrillary acidic protein (GFAP), a very specific marker of astrocytes.

Two types of astrocytes have been classically described by location and morphology. Protoplasmic astrocytes are typically found in gray matter and have thick extensively branched processes, while fibrous astrocytes found in the white matter have long straight processes. Astrocytes isolated from the optic nerve have been described antigenically as Type 1 and Type 2 on the basis of their staining for GFAP and the surface marker A2B5. Originating from two different developmental lineages and at separate times, Type 1 astrocytes only stain for GFAP, while Type 2 astrocytes stain for both A2B5 and GFAP. Astrocytes provide a conducive environment for axon growth, which is an important aspect of nerve regeneration. Thus, the survival and differentiation of astrocytes are important factors in the ability of neural cells and tissue to survive and regenerate. Silver et al., U.S. Pat. No. 5,202,120, describe a method using activated astrocytes to promote regeneration of axons. However, this method is disadvantageous in that it requires a supply of astrocytes, such as by autologous transplant.

SUMMARY OF THE INVENTION

It is one object of the present invention to provide methods and compositions capable of inducing the growth of neural cells. It is another object of the present invention to provide methods and compositions suitable for the generation of nerve cells and nerve tissue, and for the repair of neural defects. In a preferred embodiment of the present invention, the method and compositions of the present invention are useful for inducing growth of astrocytic cells.

In one embodiment, the present invention provides a method of inducing growth of neural cells which comprises administering to a mammal at a site of neural depletion, damage or defect, an effective amount of a recombinant human BMP (rhBMP) in admixture with a pharmaceutically acceptable vehicle. The BMP is preferably selected from the group consisting of BMP-2, BMP-4, BMP-5, BMP-6, BMP-7 and heterodimers of BMP-2/6 and BMP-2/7.

In another embodiment, the present invention comprises a method of treating a mammal having a neural defect, neural damage or a neural condition, which method comprises administering to said mammal at a site of neural depletion, defect or damage, a nerve-regenerating amount of rhBMP in combination with a suitable matrix. The BMP is preferably selected from the group consisting of BMP-2, BMP-4, BMP-5, BMP-6, BMP-7 and heterodimers of BMP-2/6 and BMP-2/7. Most preferred are BMP-2, BMP-4 and BMP-2/6 and BMP-2/7 heterodimers.

In a preferred embodiment, the present invention comprises a device for nerve replacement. The device preferably employs a matrix or carrier capable of maintaining the BMP in a desired location and orientation to allow regeneration of neural tissue. The BMP is adsorbed onto the matrix. The matrix may be made of any suitable carrier material known in the art. Preferably, the matrix is comprised of a suitable material selected from the group consisting of collagen, fibrin tissue adhesives, and components of normal endoneurial sheaths. These components include laminin, hyaluronic acid and chondroitin sulfate proteoglycans, including versican. Tona et al., J. Histochemistry and Cytochemistry, 41:593–599 (1993). In the most preferred embodiment, the matrix is comprised of cross-linked collagen. The collagen may be in any suitable form, but is preferably in the form of a sponge. The collagen may be shaped into a suitable shape for regeneration of nerve tissue. The BMP-adsorbed matrix may be applied to an artificial nerve replacement vessel which contains the matrix and BMP. The artificial nerve replacement vessel is preferably in the form of tubing or stent, such as vented silastic tubing.

DETAILED DESCRIPTION OF THE INVENTION

The present inventors have surprisingly found that the BMPs, particularly BMP-2, BMP-10 4 and heterodimers of BMP-2/6 and BMP-2/7 may be used to enhance nerve regeneration. Nerve cells do not ordinarily proliferate after injury, and physiologic repair using microsurgical techniques often result in imperfect functional results, despite optimal care. Nerve tissue must become neovascularized prior to repair. However, neovascularization occurs much later in nerves than in other biologic systems, slowing initial axonal repair, and often facilitating irreparable and time-dependent motor endplate atrophy. Further, the faster forming fibrotic scar tissue may prevent the success of naturally occurring nerve regeneration. Consequently, the use of BMPs to enhance or accelerate nerve repair provides a method for improving nerve repair where it might not otherwise occur.

The DNA sequences of BMPs are known and have been described as follows: BMP-2 (sometimes referred to as BMP-2A) and BMP-4 (sometimes referred to as BMP-2B), U.S. Pat. No. 5,013,649; BMP-3 U.S. Pat. No. 5,116,738; BMP-5, U.S. Pat. No. 5,106,748; BMP-6, U.S. Pat. No. 5,187,076; BMP-7, U.S. Pat. No. 5,141,905; BMP-8, PCT Publication No. WO91/18098; BMP-9, PCT Publication No. WO93/00432; BMP-10, PCT Publication No. WO94/26893.

Heterodimers are described in U.S. patent application Ser. No. 07/787,496, now abandoned filed on Apr. 7, 1992. The disclosure of the above references are hereby incorporated herein by reference as if fully reproduced herein.

Recombinant human BMP, such as rhBMP-2, may be made for use in the method of the invention by expressing the DNA sequences encoding a BMP in a suitable transformed host cell. For example, using known methods, the DNA encoding BMP-2 may be linked to an expression vector such as pED (Kaufman et al., Nucleic Acids Res. 19, 4484–4490 (1991)), transformed into a host cell, and protein expression may be induced and maximized. Of course, degenerate DNA sequences encoding human BMP may also be employed to produce rhBMP, as can DNA sequences encoding allelic variants of BMP.

Any suitable expression vector may be employed to produce rhBMP, such as rhBMP-2, for use in the present invention. For mammalian expression, numerous expression vectors are known in addition to the pED vector mentioned above, such as pEF-BOS (Mizushima et al., Nucleic Acids Res. 18, 5322 (1990)); pXM, pJL3 and pJL4 (Gough et al., EMBOJ. 4, 645–653 (1985)); and pMT2 (derived from pMT2-VWF, A.T.C.C. #67122; see PCT/US8700033). Suitable expression vectors for use in yeast, insect, and bacterial cells are also known. Construction and use of such expression vectors is well within the level of skill in the art. Recombinant BMP, such as rhBMP-2, may also be produced using a chimeric DNA sequence which encodes for a mature BMP operably linked to a propeptide from a different BMP. For example, see U.S. Pat. No. 5,168,050, the disclosure of which is hereby incorporated by reference.

Suitable host cells for production of BMPs useful in the present invention include, for example, mammalian cells such as Chinese hamster ovary (CHO) cells, monkey COS cells, mouse 3T3 cells, mouse L cells, myeloma cells such as NSO (Galfre and Milstein, Methods in Enzymology 73, 3–46 (1981)), and the like. RhBMP may also be produced by transformation of yeast, insect, and bacterial cells with DNA sequences encoding BMP, induction and amplification of protein expression, using known methods. When produced in bacterial cells, it may be necessary to solubilize the bone morphogenetic protein.

Recombinantly produced BMP, such as rhBMP-2, must be purified from culture medium or cell extracts for use in the present invention. Culture medium or cell extracts containing rhBMP may be concentrated using a commercially available protein concentration filter, for example, an Amicon or Millipore Pellicoll ultrafiltration unit. Following the concentration step, the concentrate can be applied to a purification matrix such as a gel filtration medium. Alternatively, an anion exchange resin can be employed, for example, a matrix or substrate having pendant diethylamioethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. The purification of BMP from culture supernatant may also include one or more column steps over such affinity resins as lectin-agarose, heparin-toyopearl® or Cibacrom blue 3GA Sepharose®; or by hydrophobic interaction chromatography using such resins as phenyl ether, butyl ether, or propyl ether; or by immunoaffinity chromatography. Finally, one or more reverse-phase high performance liquid chromatography (RP-HPLC) steps employing hydrophobic RP-HPLC media, e.g., silica gel having pendant methyl or other aliphatic groups, can be employed to further purify BMP for use in the present methods. Some or all of the foregoing purification steps, in various combinations, can be employed to provide a substantially homogeneous isolated recombinant protein.

BMPs, such as rhBMP-2, can be used in the method of the invention for the in vivo treatment of mammals by physicians in a variety of disease conditions. These conditions include diseases of the peripheral nervous system, such as peripheral nerve injuries, peripheral neuropathy and localized neuropathies, and central nervous system diseases, such as Alzheimer's, Parkinson's disease, Huntington's disease, amyotrophic lateral sclerosis, and ShyDrager syndrome. Further conditions which may be treated in accordance with the present invention include mechanical and traumatic disorders, such as spinal cord disorders, head trauma and cerebrovascular diseases such as stroke. BMPs may be used to increase the regeneration of nerve cells and nerve tissue in order to enhance or accelerate the healing of such disorders.

In accordance with the method of the invention, BMP, such as rhBMP-2, may be administered alone, in combination with other BMPs, or in combination with other therapies. For example, rhBMP-2 may be efficaciously combined with a cytokine, lymphokine, growth factor, or colony stimulating factor, in the treatment of neural diseases. Exemplary cytokines, lymphokines, growth factors, and colony stimulating factors for use in combination with BMP in accordance with the method of the invention include, without limitation, EGF, FGF, interleukins 1 through 12, M-CSF, G-CSF, GM-CSF, stem cell factor, erythropoietin, and the like. In addition, the BMPs may be combined with neurotrophic factors such as CNTF, LIF, IL-6 and insulin-like growth factors [IGFs]. Additionally, proteins normally found in the neural environment may be added to the BMPs in accordance with the present invention. These may include laminin, hyalauronic acid and chondroitin sulfate proteoglycans, including versican.

The BMP of the present invention may be administered employing a matrix capable of maintaining the BMP in a desired location and orientation to allow regeneration of neural tissue. The BMP may preferably be adsorbed onto the matrix. The matrix may be made of any suitable material known in the art. Such materials include a suitable materials selected from the group consisting of collagen, fibrin tissue adhesives and components of normal endoneurial sheaths, including laminin, hyalauronic acid and chondroitin sulfate proteoglycans, including versican. The matrix may preferably be porous, so as to allow the influx, migration, differentiation and proliferation of cells need for regeneration of neural tissue. In one preferred embodiment, the matrix is comprised of cross-linked collagen. The collagen may be in any suitable form, but is preferably in the form of a sponge. The collagen may be shaped into a suitable shape for regeneration of nerve tissue. In another preferred embodiment, the matrix comprises bioerodible particles, such as polymers of lactic acid (PLA), polymers of glycolic acid (PGA), and co-polymers of lactic acid and glycolic acid (PLGA). Also useful as the matrix are polymers of polyorthoesters. The matrix may comprise materials to promote the formation of neural tissue, such as fibrin, or vein graft.

The BMP-adsorbed matrix is then applied to an artificial nerve replacement vessel, preferably in the form of tubing or stent, such as vented silastic tubing. The artificial nerve replacement vessel may be comprised of any material which will hold the BMP-adsorbed matrix in place and allow for regeneration of nerve tissue. In one embodiment, autologous vein graft may be used as the nerve replacement vessel. The artificial nerve replacement vessel may comprise a resorbable material, such as polymers. In some preferred embodiments, the matrix may also serve as the artificial nerve replacement vessel.

Pharmaceutical compositions suitable for use in the method of the present invention may contain, in addition to the BMP, pharmaceutically acceptable carriers, diluents, fillers, salts, buffers, stabilizers, and/or other materials well known in the art. The term "pharmaceutically acceptable" means a non-toxic material that does not interfere with the effectiveness of the biological activity of the active ingredient(s). The characteristics of the carrier or other material will depend on the route of administration.

Administration of BMP, such as rhBMP-2, in the method of the invention can be carried out in a variety of conventional ways. For regeneration of nerve tissues, treatment of neural defect or nerve damage, topical administration of BMP is preferred. In the most preferred mode of administration, BMP is adsorbed to a biocompatible matrix and applied to an artificial nerve replacement vessel. The biocompatible matrix is preferably made of collagen, and may be in the form of a sponge, sheets or mats, or closely packed particles. The artificial nerve replacement vessel may be in the form of a tube or stent. Other materials suitable for artificial nerve replacement vessel will be apparent to those skilled in the art. In a preferred embodiment, the artificial nerve replacement vessel comprises vented silastic tubing containing the BMP-adsorbed matrix. In another preferred embodiment, the artificial nerve replacement vessel comprises autologous vein graft. In some preferred embodiments, the same material may serve as both the matrix and the artificial nerve replacement vessel.

The amount of BMP useful in the method of the present invention will depend upon the nature and severity of the condition being treated, and on the nature of prior treatments which the patient has undergone. Ultimately, the attending physician will decide the amount of BMP with which to treat each individual patient. It is contemplated that the various pharmaceutical compositions of the present invention should contain about 0.1 µg to about 100 mg, preferably about 0.1 µg to 100 µg of BMP per kg body weight. The actual dosing regimen will be determined by the attending physician considering various factors which modify the action of drugs, e.g., the condition, body weight, sex and diet of the patient, the severity of the condition, time and method of administration and other clinical factors.

In practicing the method of treatment of this invention, a therapeutically effective amount of BMP is administered to a mammal having such a disease state. The term "therapeutically effective amount" means the total amount of each active component of the method that is sufficient to show a meaningful patient benefit, i.e., healing of chronic conditions or increase in rate of healing. For example, a nerve-regenerating amount of a bone morphogenetic protein is that amount of protein which, when adsorbed to a suitable matrix carrier and implanted at a site of nerve damage, defect or depletion, will allow the regeneration of nerve tissue and/or amelioration of the neural damage, defect or depletion. When applied to an individual active ingredient, administered alone, the term refers to that ingredient alone. When applied to a combination, the term refers to combined amounts of the active ingredients that result in the therapeutic effect, whether administered in combination, serially or simultaneously. A therapeutically effective dose of BMP for practice of the method of this invention is contemplated to be in the range of about 0.1 µg to about 100 mg per kg body weight per application. Generally, administration will be initiated at the low end of the dosing range initially, and the dose will be increased over a preselected time course until a positive effect is observed. Subsequently, incremental increases in dosage will be made limiting such incremental increases to such levels that produce a corresponding increase in effect, while taking into account any adverse affects that may appear.

The duration of intravenous therapy using the method of the present invention will vary, depending on the severity of the disease being treated and the condition and potential idiosyncratic response of each individual patient. It is contemplated that the duration of each application of the BMP will be in the range of 12 to 24 hours of continuous administration. Ultimately the attending physician will decide on the appropriate duration of therapy using the method of the present invention.

In accordance with the method of the invention, neural regeneration may be achieved in mammals by administration of a nerve-regenerating amount of BMP, such as rhBMP-2, in admixture with a pharmaceutically acceptable vehicle. For the purposes of the present invention, a nerve-regenerating amount of BMP, such as rhBMP-2, in accordance with the present invention is that amount of the protein necessary to cause regeneration of nerve. The nerve regeneration may be measured by weight or volume of the nerve tissue present. It is contemplated that suitable host cells, transformed to express BMP, may also be administered to the patient in order to improve the growth or survival of neural cells or tissue.

The following examples are illustrative of the present invention, and are not limiting in any manner.

Parenteral formulations of BMP will be in the form of pyrogen-free, parenterally acceptable aqueous solutions. The preparation of such parenterally acceptable protein solutions, having due regard to pH, isotonicity, stability, and the like, is within the skill in the art. A preferred parenteral formulation should contain, in addition to BMP, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition according to the present invention may also contain stabilizers, preservatives, buffers, antioxidants, or other additive known to those of skill in the art.

When administered topically, the BMP of the present invention may be in the form of a pyrogen-free, topically acceptable liquid or semi-solid formulation such as an ointment, cream, lotion, foam or gel. The preparation of such topically applied formulations is within the skill in the art.

EXAMPLE I. BMP EFFECTS ON NEURAL CELLS

Example IA. Cell Culture

Balb c/SFME (Serum-Free Mouse Embryo) cells were obtained from the American Type Culture Collection (CRL 9392) and were grown as previously described (Sakai et al., PNAS:USA, 87:8378–8382 (1990)) in DME/F12 (1:1) medium containing bovine insulin, 10 µg/ml (Eli Lilly); human transferrin, 25 µg/ml (Collaborative Research); human high density lipoprotein, 20 µg/ml (sigma); human epidermal growth factor, 100 ng/ml (PeproTech); bovine plasma fibronectin, 20 µg/ml (GIBCO); sodium selenite, 10nM (GIBCO); penicillin-streptomycin (10 U/ml), 1-glutamine (4mM) and 4-(2-hydroxy-ethyl) - piperazine-ethanesulfonic acid, pH 7.4 (15 mM).

Cells were passaged using trypsin/EDTA and soybean trypsin inhibitor (1 mg/ml) in a volume ratio of 1:2 and used between passages 19 and 50. Cells were counted, unless otherwise stated, with a Coulter Diagnostics counter.

Example IB Growth and Differentiation Factors

All recombinant human proteins used were of greater than 90% purify. EGF was purchased from PeproTech (N.J.); recombinant human Activin-A was the generous gift of Helen New; TGF-β1 was purchased from R&D Systems; BMPs were purified from CHO conditioned media through several purification steps at Genetics Institute.

Example IC. Differentiation Studies

For all immunofluorescence and FACS analysis, unless otherwise stated, cells were plated at $2.5-5\times10^4/cm^2$ and BMP-2 was added at 16–20 hrs. at the concentrations and for the length of time indicated.

Example ID. Survival Studies

Cells were washed twice in medium without EGF and then plated at $0.8-1\times10^5/cm^2$ into the same medium supplemented with various growth factors. These included BMP-2, BMP-4, BMP-5, BMP-6, BMP-7, BMP-2/6 heterodimer, BMP-2/7 heterodimer and TGF-β1. Percent viability and cell number were determined in duplicate by trypan blue dye exclusion with a hemocytometer at 44–48 hrs., counting a minimum of 400 cells per sample. Percent viability was calculated as total live cells divided by the total number of cells at the endpoint since cell proliferation was seen in some conditions.

Example IE. Immunofluorescent Antibody Staining

Media was removed from cells in four-well glass or plastic chamber slides (Lab Tek) and they were washed twice with PBS- Ca+2, Mg+2 free (CMF). For surface staining with the antibody A2B5 (Boehringer-Mannheim) the cells were initially fixed with 4% paraformaldehyde for 10 minutes, washed with PBS and then incubated with 1% rabbit serum in PBS to block nonspecific binding. The antibody was diluted in 1% rabbit serum in PBS and incubated for 1 hour then the cells were washed in 1 % rabbit serum in PBS before detection with a biotinylated rabbit anti-mouse antibody followed by a streptavidin-FITC (Zymed) conjugate. For further double staining experiments or single internal staining for GFAP, cells were fixed in acetone/methanol (50:50) at -20° C. for 10 minutes. Permeabilization and blocking was performed with 0.2% Triton X-100 and 1% of either goat or rabbit serum in PBS depending on the second step reagent. Primary antibodies were either rabbit polyclonals (1:200) or mouse monoclonals (5 µg/ml) as indicated, diluted in either 1 % goat or rabbit serum in PBS, respectively, and incubated for one hour. Detection was with either a secondary biotinylated antibody (Zymed) and streptavidin phycoerythrin (PE) (Zymed) or a conjugated antiIgG1-PE antibody (Zymed). Cells were examined with either a Zeiss Axiophot or an Olympus BH2-RFC microscope equipped with epifluorescent optics and photographed with Ektachrome 1600 ASA film.

Example IF. Facs Analysis

For these experiments, the cells were washed once with PBS and once with EDTA/salts before incubation in EDTA/salts for 20 minutes at room temperature. Cells were then removed by gentle pipetting on the surface of the plates. The plates were washed with EDTA/salts and combined with the cells which were then spun down, washed once more with PBS and then counted. $1\times10^6$ cells were used for each antibody incubation. For A2B5 surface staining at 4C, the cell pellet was first incubated with 50 µl heat inactivated rabbit serum to block nonspecific binding and then with the A2B5 antibody (Boehringer-Mannheim) or control class specific IgM at 5 µg/ml diluted in 1 % rabbit serum/PBS for one hour. Detection was with a directly conjugated anti-IgM-PE (Zymed). For further double staining experiments or single internal staining for GFAP, the cells were fixed in 0.25% paraformaldehyde at 4° C. for one hour, spun down and then resuspended in 1 ml of 0.2% Tween 20 in PBS/Azide and incubated at 37° C. for 15 minutes. 1 ml of 2% heat inactivated rabbit serum/PBS was added and the cells were spun down. The pellet was resuspended in 50 µl of rabbit serum and then the primary antibodies and class-specific controls were diluted in 100 µl of 1% rabbit serum in PBS at 5 µg/ml. Final detection was with directly conjugated anti-IgG1-FITC antibody (Zymed, Fisher Biotech). Cells were washed with 1% rabbit serum, 0.2% Tween 20 in PBS/Azide, then with PBS and then finally resuspended in 1 % paraformaldehyde. FACS analysis was performed on a FACScan (Becton Dickinson, San Jose, Calif.) using a 15 mw, 488 nm air-cooled argon ion laser for fluorochrome excitation. Fluorescence emission was measured in the standard FACScan configuration: 530 nm (FITC__, 585 nm (PE) and>650 nm (red fluorescence).

Data was acquired and analyzed on a Hewlett Packard 340C computer system, using LYSYS II software (Becton Dickinson, San Jose, Calif.). Isotype controls were run for each sample and gates were set for single staining experiments such that they included no more than 3% of the cells.

Example IG. Western Analysis

Cells were plated into duplicate wells of a 6-well dish at $2.5\times10^4/cm^2$ and the appropriate BMP or TGF-µ01 was added at 1, 10 and 100 ng/ml at 16 hours. After 44 hours the cells were harvested. One well was trypsinized and counted and the second was washed with PBS, the cells scraped into ice-cold PBS containing 1mM Pefabloc (water-soluble protease inhibitor from Boehringer-Mannheim) and centrifuged at 400×G. 1–2 volumes of 0.1% Triton X-100, 1 mM Pefabloc, 0.125 M T ris base, pH 6.8, DNAse at 250 U/ml was added to the cell pellets and mixed. Finally 0.5% SDS and 20mM DTT were added to each. Based on the cell counts of the duplicate wells, the equivalent volume containing $5\times10^5$ cells of each condition was loaded in each lane of a 12%, 1 mm Laemlli mini-gel (Novex). Bovine GFAP was also loaded at 10 and 100 ng. After running, the gel was transferred at 300 mAmps×1 hour in the presence of 0.05% SDS to 0.45 µ nitrocellulose. The blot was air dyed, fixed in 1% KOH, washed and blocked in 0.5% Tween 20 in TBS (20 mM Tris, 500 mM NaCl, pH 8.5) then incubated in a 1:1000 dilution of GFAP antiserum (BTI) overnight. After washing in 0.5% Tween 20 in TBS, the blot was incubated in a 1:3000 dilution of goat anti-rabbit HRP×1 hour and then developed by Enhanced Chemiluminescence (Amersham kit). Briefly, the blot was washed in TBS-Tw20 followed by TBS, incubated in a 1:1 mixture of reagents A and B for 1 minute and then exposed to film and developed.

RESULTS

Treatment of SFME cells with TGF-β1 or serum resulted in distinct morphological changes accompanied by expression of the astrocyte-specific differentiation marker GFAP (Sakai et al., supra). TGF-β1 treatment resulted in an elongated bipolar cell type with cytoplasmic processes at both ends which stained for GFAP. By contrast, fetal calf serum (FCS)-treated cells were larger in size, with a highly branched filament network which stained very strongly for GFAP.

Treatment of SFME cells with BMP-2, 4, 5, 6, 7 and BMP-2/6 and 2/7 heterodimer at 10 ng/ml resulted in a dramatic morphological change in their appearance, accompanied by expression of GFAP. The cells acquired many long cytoplasmic processes typical of primary astrocytes in culture. Overall, the intensity of GFAP staining observed with BMPs and calf serum was much greater than that observed for TGF-β. BMP-2 and BMP 2/7 heterodimer induced a cell type with the larger morphology, similar to what was seen with calf serum, while BMP-7 induced a morphology which was more fibrous in nature. It is possible that these morphologies reflect either phenotypic differences in the induced cell type (Type 1 vs. Type 2 astrocytes) or varying levels of GFAP or other cytoskeletal proteins. Control cells have a fibroblast-like appearance and do not stain for GFAP.

In order to accurately measure the level of GFAP expression induced by BMP, as well as compare the activity to that of TGF-β, a quantitative assay by fluorescence activated cell sorting was established. The cells were treated with 10 ng/mn of each BMP, TGF-β1 and Activin and 10% calf serum. The data were analyzed by percent of the population responding and mean fluorescence intensity.

The percentage of the population responding is reflective of the number of cells expressing GFAP, independent of the level of expression. BMP-2, 4, 5, 6, 7, 2/6 heterodimer and 2/7 heterodimer, TGF-β and calf serum significantly induce the expression of GFAP compared with the control. Activin, another member of the TGF-β superfamily, also has no effect. The BMP-2/6 and 2/7 heterodimers are most effective in this parameter, resulting in approximately 65 to 72% responsive cells. BMP-2, 4, TGF-β1 and fetal calf serum treatments result in approximately 53 to 58% responsive cells; BMP-5, 6 and 7 treatments result in approximately 30 to 40% responsive cells.

Mean fluorescence intensity (MFI) is indicative of the level of GFAP expression; the higher the mean fluorescence, the greater the level of GFAP expressed. BMP-2/6 and 2/7 heterodimer induced cells have a mean fluorescence approximately 8-fold greater than that of the TGF-β1 induced cells. BMP-2, 4, 5, 6, and 7 induced cells have a mean fluorescence approximately 2 to 4-fold greater than that of calf serum. TGF-β and calf serum all give values significantly higher than the control.

In order to compare the ability of BMPs and TGF-β1 to induce GFAP, BMP-2, BMP-6, BMP-2/6 heterodimer and TGF-β1 were tested over a concentration range of 0–10 ng/ml and the FACS assay was used for quantitation of GFAP expression. The concentration at which each factor gave a GFAP mean fluorescence value of 5 (10-fold over the control of 0.5) was used to compare relative activities. In terms of relative activity compared to TGF-β1, BMP-2/6 heterodimer was approximately 18 fold more active and BMP-2 and BMP-6 were aproximately 3–4 fold more active. BMP-2 and BMP-2/6 induced detectable levels of GFAP in the 0–0.08 ng/ml range while the first detectable GFAP increase with TGF-β1 is in the 0.4–2 ng/ml range.

Western analysis also confirmed the higher levels of GFAP produced by SFME cells after exposure to BMPs. In BMP or TGF-β1 treated cellular extracts, the polyclonal GFAP antibody used for detection specifically recognizes a protein in the 40–50 kD range, which runs slightly below the 52 kD bovine GFAP standard. The broad molecular weight range observed is probably the result of proteolysis. There was a dose-dependent increase in protein levels with BMP-2 and BMP-6 treatment from 1–100 ng/ml. GFAP induced by TGF-β treatment was maximal at a 10 ng/ml dose and is approximately equal to that seen with only 1 ng/ml of BMP-2 . This level could not be increased even at a 100 ng/ml dose. BMPs induced higher levels of GFAP than TGF-β1.

Treatment of SFME cells with BMPs results in conversion of the "fibroblast-like" cells into two distinct GFAP-positive morphologies. One large, flat cell type with few processes is reminiscent of a protoplasmic type of astrocyte; another with very long cytoplasmic processes is characteristic of a fibrous astrocyte.

These cells were further characterized by double immunofluorescent antibody staining for A2B5 and GFAP. In the BMP-2/6 population, both Type 1 and Type 2 astrocyte lineage cells were present. The majority of cells which stained for GFAP but not A2B5 were of the Type 1 astrocyte lineage while the cells which stained for both A2B5 and GFAP were of Type 2 astrocyte lineage. Control cells stained for A2B5 on their surface, but did not stain for GFAP.

In order to quantitate the populations of cells seen by immunofluorescent staining, we employed double staining FACS analysis. The data in Table 1 is expressed as an average of at least three experiments± standard deviation. Control cells were approximately 37% A2B5 positive. Control cells did not stain positively for the astrocyte lineage markers. BMP-2, 6 and 2/6 treated cells did not stain only for A2B5, but did consist of the two astrocyte lineage populations. Greater than 60% were positive for GFAP alone indicating that they were of Type 1 lineage and about 18% were positive for both A2B5 and GFAP, indicating that these were of Type 2 lineage. TGF-β1 treatment also resulted in a similar size population of Type 2 lineage cells (approximately 14%), but only approximately 40% positive population of Type 1 lineage cells. There also remained a small population of cells (approximately 7%) which single stained for A2B5. Overall, treatment of SFME cells with either BMPs or TGF-β1 resulted in the loss of expression of A2B5 which cannot be totally accounted for in the A2B5/GFAP population.

TABLE 1

| | ASTROCYTES | | |
| --- | --- | --- | --- |
| | A2B5 | TYPE 1 GFAP | TYPE 2 A2B5/GFAP |
| Control | 37.13 ± 18.66 | 0.15 ± 0.19 | 1.18 ± 0.67 |
| BMP-2 | 0.39 ± 0.54 | 60.49 ± 3.71 | 19.89 ± 3.31 |
| BMP-6 | 0.25 ± 0.43 | 59.28 ± 1.28 | 17.89 ± 3.19 |
| BMP-2/6 | 0.42 ± 0.38 | 65.07 ± 7.33 | 18.37 ± 5.49 |
| TGF-β1 | 7.05 ± 1.02 | 39.72 ± 3.02 | 14.23 ± 3.04 |

SFME Cell Survival Study

EGF is required for survival of SFME cells and other factors such as FGF and TGF-β cannot substitute for it. In the absence of EGF, SFME cells were treated with BMP-2, 7, 2/7 heterodimer, TGF-β1 and activin. Activin has been shown to be a nerve cell survival molecule for P19 cells. Schubert et al., Nature344:868–870 (1990). After 48 hours in the absence of EGF, there were only about 30% surviving cells, and an overall decrease in cell number. Addition of EGF resulted in approximately 95% cell survival rate accompanied by a 5-fold increase in cell number. Cells treated with BMP-2, BMP-7 and BMP-2/7 heterodimer maintained a cell number approximately 70–80% of the seeding density. However the cells did not proliferate. BMP-2 treated cells not only survived but also apeared to have differentiated. The survival rate was approximately 80–85%. Treatment of cells with either TGF-β1 or Activin resulted in survival rates of<10% and at least a 10-fold decrease in cell number. Higher concentrations of TGF-β1 did not increase survival.

EXAMPLE II. PERIPHERAL NERVE REGENERATION IN MAMMALS USING BMP-2

A. Preparation of Collagen Sponge

Collagen sponges (Collastat<sup>R</sup>, Vitaphore Wound Healing, Inc.) were cut in approximately 2×2×18 mm lengths, washed extensively in sterile glass distilled water, lyophilized, ethylen oxide sterilized and degassed prior to addition of BMP-2.

0.5 µg of BMP-2 in 45% Acetonitrile, 0.1% trifluoroacetic acid was evenly distributed over the length of each prepared sponge. These were then placed in a tube, frozen in liquid nitrogen and lyophilized. Control implants were prepared the same way except with 45% Acetonitrile, 0.1% Trifluoroacetic acid buffer without BMP-2.

After lyophilization, the BMP-2 loaded and control sponges were placed inside of approximately 1.6×20 mm lengths of sterile vented silastic tubing. All manipulations were performed under sterile conditions. Excess tubing at either end of the implant was removed in the operating room prior to surgery.

The sciatic nerve of 6 Lewis' rats were severed. Vented silastic or biodegradable stents, 1.6 mm internal diameter× 17 mm long, were inserted. Stents contained collagen matrix carrier with or without rhBMP-2. The collagen matrix carrier was composed of collagen sponge (Collastat) (approximately 1.5 mm×15 mm). Animals with the sciatic nerve severed and tied back to prevent reattachment served as positive controls. The unoperated hind limb served as age-matched negative controls.

The stents were applied microscopically and anastomosed to the severed nerve endings of the sciatic nerve. The nerve endings were inserted into the stent for 1 mm at each end, leaving a 15 mm gap. Animals were tested for electrical return of function at 6, 8 and 12 weeks post implantation. Compound muscle action potentials (CMAP) were examined, which provided a reliable, reproducible, transcutaneous procedure which is an accurate for determining the degree of tunctional return. Amplitude and latency are age-dependent and directly proportional to the number of reinnervated axons/motor endplates.

Animals were sacrificed for pathological examination at 12 weeks PI. Stains included H&E, Silver, Luxol-fast blue and S100. Unbiased quantification of the proximal, central and distal elements within the stent were performed. Stents placed within the subcutaneous tissues of several rats served as controls for the stains.

Results showed good nerve regeneration across the 15 mm nerve defect in 4 of 6 animals treated with 0.5 ug per device of BMP-2 deposited on Collastat sponge after 12 weeks. The controls without BMP-2 revealed no growth across the 15 mm nerve defect.

We claim:

1. A nerve replacement device comprising an artificial nerve replacement vessel which contains a composition comprising a bone morphogenetic protein in an amount sufficient to promote the growth of astrocyes and a suitable matrix carrier, said bone morphogenetic protein being selected from the group consisting of BMP-2, BMP-4, BMP-5, BMP-6, BMP-7 and heterodimers of BMP-2/6 and BMP-2/7.

2. The device of claim 1, wherein the bone morphogenetic protein is selected from the group consisting of BMP-2, BMP-4, BMP-2/6 heterodimers and BMP-2/7 heterodimers.

3. The device of claim 1, wherein the matrix comprises a suitable material selected from the group consisting of collagen, fibrin tissue adhesives, laminin, hyalauironic acid and chondroitin sulfate proteoglycans.

4. The device of claim 3, wherein the matrix comprises collagen.

5. The device of claim 4, wherein the collagen is in the form of a sponge.

6. A nerve replacement device according to claim 5, wherein said bone morphogenetic protein is BMP-2.

7. The device of claim 1, wherein the artificial nerve replacement vessel comprises vented silastic tubing.

8. A nerve replacement device according to claim 1, wherein said bone morphogenetic protein is BMP-2.

9. A method of using the nerve replacement device of claim 1, comprising implanting the devide at a site in need of peripheral nerve repair.

10. A method of inducing formation of astrocytes in a suitable cell population which method comprises administering to said cell population an effective amount of a bone morphogenetic protein in admixture with a pharmaceutically acceptable vehicle, said bone morphogenetic protein being selected from the group consisting of BMP-2, BMP-4, BMP-5, BMP-6, BMP-7 and heterodimers of BMP-2/6 and BMP-2/7.

11. The method of claim 9, wherein the bone morphogenetic protein is selected from the group consisting of BMP-2, BMP-4, BMP-2/6 heterodimers and BMP-2/7 heterodimers.

12. The method of claim 10, wherein the bone morphogenetic protein is adsorbed to a suitable matrix.

13. The method of claim 11, wherein the matrix comprises collagen is in the form of a sponge.

14. The method of claim 13, wherein said bone morphogenetic protein is BMP-2.

15. The method of claim 12, wherein the matrix is contained within an artificial nerve replacement vessel.

16. The method of claim 15, wherein the artificial nerve replacement vessel comprises vented silastic tubing.

17. The method of claim 10, wherein said bone morphogenetic protein is BMP-2.

* * * * *